(12) United States Patent
Cicaroni Fernandes et al.

(10) Patent No.: US 12,163,008 B2
(45) Date of Patent: Dec. 10, 2024

(54) PRODUCTION AND USE OF PLASTICIZERS BASED ON 2,4-ISOMER OF FURANDICARBOXYLIC ACID DIESTERS

(71) Applicant: Braskem S.A., Camacari (BR)

(72) Inventors: Felipe Cicaroni Fernandes, Campinas (BR); Iuri Estrada Gouvea, Campinas (BR); Antonio Rodolfo, Jr., Sao Paulo (BR); Mateus Schreiner Garcez Lopes, Sao Paulo (BR)

(73) Assignee: BRASKEM S.A., Camacari (BR)

( * ) Notice: Subject to any disclaimer, the term of this patent is extended or adjusted under 35 U.S.C. 154(b) by 190 days.

(21) Appl. No.: 17/333,317

(22) Filed: May 28, 2021

(65) Prior Publication Data

US 2021/0371622 A1 Dec. 2, 2021

Related U.S. Application Data

(60) Provisional application No. 63/031,949, filed on May 29, 2020.

(51) Int. Cl.
*C07D 307/68* (2006.01)
*C08J 3/12* (2006.01)
(Continued)

(52) U.S. Cl.
CPC .......... *C08K 5/1535* (2013.01); *C07D 307/68* (2013.01); *C08J 3/12* (2013.01);
(Continued)

(58) Field of Classification Search
CPC .............................. C08K 5/175; C08J 2327/06
See application file for complete search history.

(56) References Cited

U.S. PATENT DOCUMENTS 10,301,276 B2 * 5/2019 Asikainen ................ B01J 21/04
528/306
11,566,270 B2 * 1/2023 Alexandrino ............ C12N 9/16
(Continued)

FOREIGN PATENT DOCUMENTS

WO WO2016166421 10/2016

OTHER PUBLICATIONS

International Search Report and Written Opinion dated Aug. 5, 2021 issued for International PCT Application No. PCT/IB2021/054711 filed May 28, 2021.
(Continued)

*Primary Examiner* — Catherine S Branch
*Assistant Examiner* — Huihong Qiao
(74) *Attorney, Agent, or Firm* — K&L Gates LLP

(57) ABSTRACT

The present disclosure generally relates to a compound of dialkyl ester of 2,4-furandicarboxylic acid, a method of preparing the compound, a polymer composition comprising a polymer and the compound, a method of preparing the polymer composition, a polymer product comprising the polymer composition and a method of using the compound as a plasticizer in the polymer product. The dialkyl ester of 2,4-furandicarboxylic acid of the present disclosure has greater plasticizing efficiency in a polymer composition that that of the standard phthalate and terephthalate-based plasticizers. The polymer product plasticized with the dialkyl ester of 2,4-furandicarboxylic acid may have improved flexibility, durability, processability and safety as compared to the same polymer product plasticized with conventional phthalate and terephthalate-based plasticizers.

20 Claims, 2 Drawing Sheets

(51) Int. Cl.
*C08J 3/18* (2006.01)
*C08K 5/00* (2006.01)
*C08K 5/1535* (2006.01)
*C08L 27/06* (2006.01)

(52) U.S. Cl.
CPC ............... *C08J 3/18* (2013.01); *C08K 5/0016* (2013.01); *C08L 27/06* (2013.01); *C08J 2327/06* (2013.01)

(56) References Cited

U.S. PATENT DOCUMENTS

2013/0338276 A1* 12/2013 Becker ................. C08K 5/1535
524/111
2014/0128623 A1 5/2014 Janka et al.

OTHER PUBLICATIONS

Do Carmo Cabral Sacadura et al. KT Consortium Annual Meeting Jun. 2017, 1 page.
Paasikallio et al., "Scaling up and scaling down the production . . . ", Microbial Cell Factories, vol. 16:119, No. 1, Dec. 2017, pp. 1-11.
E. H Immergut and H. F. Mark (1965), Principles of Plasticization, N. A. J. Platzer, Plasticization and Plasticizer Processes (pp. 12-24), American Chemical Society.

* cited by examiner

PRODUCTION AND USE OF PLASTICIZERS BASED ON 2,4-ISOMER OF FURANDICARBOXYLIC ACID DIESTERS

CROSS-REFERENCE TO RELATED APPLICATIONS

The present application claims priority to the application of U.S. Provisional Patent Application No. 63/031,949 filed on May 29, 2020, the disclosure of which is incorporated herein by reference in its entirety for all purposes.

TECHNICAL FIELD

The present disclosure generally relates to a compound of dialkyl ester of 2,4-furandicarboxylic acid, a process of preparing the compound, a composition comprising the compound, a method of preparing the composition comprising the compound, a polymer product comprising the compound as a plasticizer, and a method of preparing the polymer product.

BACKGROUND

Plasticizers are widely used as additives in the polymer industry thanks to the ease of controlling the physical properties of polymer materials, such as the flexibility, durability and processability, by adding the plasticizers to and adjusting their content in the polymer materials. This class of additives is particularly exploited in the polyvinyl chloride (PVC) resin industry, which according to 2017 data accounts for about 90% of all plasticizer consumption worldwide. Thus, plasticizers play a crucial role in the PVC industry segment, especially from the point of application, by allowing an inherently rigid material to be transformed into highly flexible products.

Plasticizers are responsible for making PVC one of the most versatile thermoplastics from an application point of view. For example, PVC resins may have different levels of flexibility depending on the content of the plasticizer: while rigid PVC materials (elongation at break <15%) normally have no plasticizer in the formulation, semi-rigid materials (elongation at ~280%) may have up to a quarter by mass of plasticizer. The plasticizer content reaches expressive levels in flexible and very flexible applications (elongation>380%), where a PVC formulation may have by weight more plasticizer than polymer.

Within the classes of molecules with properties suitable to act as plasticizers, phthalic diesters have traditionally been exploited by combining technical and performance characteristics with a low production cost. These conventional plasticizers include, for example, phthalate-derived plasticizers such as di-2-ethylhexyl phthalate (DEHP), diisononyl phthalate (DINP) and diisodecyl phthalate (DIDP). Phthalate-derived plasticizers currently comprise about 65% of all global plasticizer production. Despite their predominant historical use, plasticizers derived from phthalic anhydride face a serious crisis associated with environmental and health problems caused by them. Specifically, di (2-ethylhexyl) phthalate (DEHP) and its metabolite mono-2-ethylhexyl phthalate have been recognized in several studies over the past three decades as endocrine disruptors, negatively affecting the male reproductive system, as well as inducing problems during fetal development and obesity.

Faced with risks demonstrated in numerous independent studies, government agencies have been imposing a number of regulations to control, reduce or even ban the use of phthalate-derived plasticizers on certain items. For example, the European Commission has included DEHP and other phthalate derivatives in the REACH list. Since 2007, DEHP and other phthalate derivatives, such as benzyl butyl phthalate (BBP), dibutyl phthalate (DBP) and diisobutyl phthalate (DIBP), have been banned from mouth-wrapping food, toys and children's articles. In 2015, these restrictions were extended to other general purpose items, further pressuring the PVC market to develop alternative plasticizers. Similarly, the U.S. Consumer Product Safety Commission, moved by prior rulings by the California government, approved a regulation in 2017 to alert consumers to the use of these compounds. Thus, all materials containing more than 0.1% by weight of phthalates require a label warning of their presence in the formulation. For this reason, several of these phthalates are commonly called "labelled plasticizers".

SUMMARY

One aspect of the present disclosure is a compound of dialkyl ester of 2,4-furandicarboxylic acid having a chemical structure of Formula I:

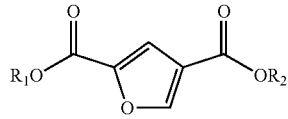

$R_1$ and $R_2$=alkyl radical of $C_4$-$C_{13}$ monohydric aliphatic primary alcohols Formula I.

wherein $R_1$ and $R_2$ each represent an alkyl radical of a $C_4$-$C_{13}$ monohydric aliphatic primary alcohol including, but not limited to, 2-ethylhexanol, ethylhexanol, n-butanol, isononyl alcohol, isobutanol, isodecyl alcohol, 2-propylheptanol, $C_6$-$C_1$ linear alcohols, tridecyl alcohol, isooctyl alcohol, amyl alcohol and other structural isomers of the alcohols with the general structure described above.

In one embodiment, $R_1$ and $R_2$ are two different alkyl radicals. In another embodiment, $R_1$ and $R_2$ are preferably the same alkyl radical. In yet another embodiment, $R_1$ is a linear alkyl radical or a branched alkyl radical. In yet another embodiment, $R_2$ is a linear alkyl radical or a branched alkyl radical.

Another aspect of the present disclosure provides a process of preparing a compound of dialkyl ester of 2,4-furandicarboxylic acid having a chemical structure of Formula I shown above, the process comprises synthesizing 2,4-furandicarboxylic acid (2,4-FDCA) or a derivative thereof; and esterifying the 2,4-FDCA or the derivative thereof with an alcohol to obtain a dialkyl ester of 2,4-furandicarboxylic acid having the chemical structure of Formula I shown above, wherein $R_1$ and $R_2$ each represent an alkyl radical of a $C_4$-$C_{13}$ monohydric aliphatic primary alcohol including, but not limited to, 2-ethylhexanol, ethylhexanol, n-butanol, isononyl alcohol, isobutanol, isodecyl alcohol, 2-propylheptanol, $C_6$-$C_{11}$ linear alcohols, tridecyl alcohol, isooctyl alcohol, amyl alcohol and other structural isomers of the alcohols with the general structure described above. In one embodiment, $R_1$ and $R_2$ are the same alkyl radical or are two different alkyl radicals. The 2,4-furandicarboxylic acid diesters resulting from this process can have their properties tuned according to variations in the length and structure of the alkyl chains of the alcohol.

In another embodiment, the compound of dialkyl ester of 2,4-furandicarboxylic acid comprises isomeric $C_4$-$C_{13}$ dialkyl furandicarboxylates, with isomeric $C_4$-$C_{13}$ dialkyl groups selected from unbranched, singly, doubly, triply and quadruply branched alkyl chains, and a mixture thereof.

In another embodiment, the 2,4-FDCA or the derivative of 2,4-FDCA is synthesized from a renewable material to produce bio-based 2,4-FDCA or derivative of 2,4-FDCA. In an embodiment, the bio-based 2,4-FDCA or the derivative of 2,4-FDCA has from about 0.1% to about 99%, from about 0.1% to about 90%, from about 0.1% to about 75%, or preferably more than 90% of bio-based carbon as determined by ASTM D6866.

In another embodiment, the 2,4-furandicarboxylic acid (2,4-FDCA) is synthesized from a renewable material that permits the compound dialkyl ester of 2,4-furandicarboxylic acid to contain different levels of bio-based carbon, such as from about 0.1% to about 99%, more than about 90%, or preferably from about 29% to more than 90% of bio-based carbon, as typically measured according to ASTM D6866, depending on the source of the monohydric aliphatic primary alcohols.

In another embodiment, the process of preparing the compound of dialkyl ester of 2,4-FDCA comprises using a stoichiometric excess (5 to 100% by mole) of the plasticizing alcohol to react with 2,4-FDCA or a suitable derivative of 2,4-FDCA, optionally in the presence of a esterification catalyst such as Bronsted and Lewis acids, organic and inorganic acids, or metal catalysts such as tin (II) derivatives and metal esters such as titanium and zirconium esters and metal alkoxides such as antimony oxides and zeolites.

In another embodiment, the process of preparing the dialkyl ester of 2,4-FDCA further comprises removing the excess of alcohol by vacuum evaporation after the complete conversion of the 2,4-FDCA or a suitable derivative of 2,4-FDCA into a dialkyl ester of 2,4-FDCA.

In another embodiment, the process of preparing the compound of dialkyl ester of 2,4-FDCA further comprises removing impurities such as the titanium catalyst from the resulted dialkyl ester of 2,4-FDCA. In one embodiment, the process of preparing the compound of dialkyl ester of 2,4-FDCA further comprises dissolving the obtained compound in dichloromethane to form a solution; treating the solution with an activated charcoal to absorb impurities such as titanium catalyst to the charcoal; filtering the treated solution to remove the charcoal and the impurities absorbed to the charcoal; and evaporating the dichloromethane under vacuum.

Another aspect of the present disclosure is a composition comprising a polymer and the compound of dialkyl ester of 2,4-FDCA discussed above as a plasticizer, wherein the dialkyl ester of 2,4-FDCA compound is present in the composition in an amount of 1 to 300, more preferably 10 to 150, even more preferably 15 to 80 parts per weight of the compound per 100 parts per weight of the polymer.

In one embodiment, the composition exhibits a bio-based carbon content as determined by ASTM D6866, ranging from about 0.1% to about 90%, more than about 90%, or preferably from about 0.1% to about 75%.

In another embodiment, the polymer is selected from the group consisting of PVC, polyvinyl butyral (PVB), thermoplastic polyurethane (PU), polylactic acid (PLA), polyhydroxybutyral (PHB), polybutylene succinates (PBS), polybutylene succinate adipates (PBSA), polyethers, polysulfides, polysuldones homo- and copolymers of polystyrene (PS), polycarbonates (PC), polyalkyl methacrylates (PAMA), starch, thermoplastic starch (TPS) and combinations thereof.

In another embodiment, the polymer is polyvinyl chloride (PVC). In another embodiment, the PVC is derived from suspension, bulk, solution, emulsion or microsuspension polymerization processes.

In another embodiment, the composition further comprises one or more suitable additives typically used in polymer compositions such as light stabilizers, acid stabilizers, thermal stabilizers, UV stabilizers, fillers and reinforcements, biocides, expansion agents, demoulding additives, lubricants, flow modifiers, impact modifiers, antiblocking agents, antistatic agents, slipping agents, pigments and flame retardants.

In another embodiment, the composition further comprises an additional plasticizer selected from the group consisting of $C_4$-$C_{13}$ dialkyl phthalates, alkyl benzoates, trialkyl trimellitates, dialkyl adipates, alkyl 1,2-cyclohexanedicarboxylates, alkyl 1,3-cyclohexanedicarboxylates, alkyl 1,4-cyclohexanedicarboxylates, glyceryl esters, isosorbide ester, epoxidized vegetable oils, saturated and unsaturated fatty acid esters which may be fully or partially epoxidized, citric triesters, alkylpyrrolidones, and combinations thereof.

In another embodiment, the additional plasticizer is preferably a non-phthalate diester (also referred as ortho-plasticizers).

Another aspect of the present disclosure is a method of preparing a composition comprising a polymer and the compound of the dialkyl ester of 2,4-FDCA discussed above as a plasticizer, wherein the method comprises mixing the polymer in a powder or pellet/granule form, the dialkyl ester of 2,4-FDCA and other additives such as Ca/Zn stabilizer and stearic acid together to form a dry blend; filling the dry blend into a two roll mill; and processing the mill for more than three minutes to facilitate the plasticizer incorporation and homogenization of the composition.

Another aspect of the present disclosure provides a polymer product comprising a composition comprising a polymer and the compound of the dialkyl ester of 2,4-FDCA discussed above as a plasticizer.

In one embodiment, the polymer product is selected from the group consisting of paints, inks, adhesives or adhesive components, sealing compounds, coating compositions, lacquers, plastisols, synthetic leather, solvents, lubricating oil, floor coverings, underbody protection, fabric coatings, cables or wire insulation, extruded articles, and films. The polymer product is produced by traditional means such as calendering, extrusion, injection moulding or any other processing technique able to melt and mix effectively the additive in the composition.

In another embodiment, the polymer product exhibits a bio-based carbon content as determined by ASTM D6866, ranging from about 0.1% to about 90%, more than about 90%, or preferably from about 0.1% to about 75%.

Another aspect of the present disclosure is a method of making a polymer product comprising the composition comprising a polymer and the compound of the dialkyl ester of 2,4-FDCA as a plasticizer as discussed above, the method comprises mixing the polymer in a powder or pellet/granule form, the dialkyl ester of 2,4-FDCA and other additives such as Ca/Zn stabilizer and stearic acid together to form a dry blend; filling the dry blend into a two roll mill; processing the mill for more than three minutes to facilitate the plasticizer incorporation and homogenization of the composition; and processing the resulted homogenized composition into the polymer product by calendering, extrusion, injection moulding or any other processing technique suitable to transform the polymer composition into the polymer product.

DETAILED DESCRIPTION

Figure 1:
FIG. 1 shows the Shore A hardness of the test samples of a compound with the dialkyl esters of 2,4-FDCA of the present disclosure as a plasticizer versus comparative control samples with standard phthalate and terephthalate-based plasticizers.

Described herein are new plasticizers based on 2,4-isomer of furandicarboxylic acid diesters which may be used in polymer materials including PVC. These plasticizers may overcome one or more of the above mentioned disadvantages of existing plasticizers or at least provide a useful alternative. Also described is a cost effective process of preparing the plasticizer based on 2,4-isomer of furandicarboxylic acid diesters. This process may be cost effective as compared to that of the existing plasticizers. Also disclosed is a composition comprising the plasticizer based on 2,4-isomer of furandicarboxylic acid diesters, as well as a method of preparing such composition. Also disclosed is a polymer material comprising the plasticizer based on 2,4-isomer of furandicarboxylic acid diesters with improved or at least equal flexibility, durability, processability and safety as compared to the same material plasticized with the current existing plasticizers.

All percentages expressed herein are by weight of the total weight of the composition unless expressed otherwise. When reference herein is made to the pH, values correspond to pH measured at 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y."

Where used herein, the terms "example" and "such as," particularly when followed by a listing of terms, are merely exemplary and illustrative and should not be deemed to be exclusive or comprehensive.

The term "substantially no" as used in reference to a particular component means that any of the component present constitutes less than about 2.0% by weight, such as less than about 1.0% by weight, preferably less than about 0.5% by weight or, more preferably, less than about 0.1% by weight.

The term "plasticizer" as used herein, refers to an additive that is added to a polymer, such as polyvinyl chloride (PVC), to change the physical properties of the polymer, such as decreasing the viscosity and increasing the flexibility of the polymer to thus soften the polymer. The softening is brought about by the plasticizer dissolving in the polymer and lowering the glass transition temperature ($T_g$) of the polymer. By changing the type and concentration of the plasticizer in the polymer, the properties of the polymer can be tailored to requirements. Increasing the plasticizer concentration in the polymer increases flexibility, decreases tensile strength, and reduces hardness of the polymer. The plasticizers also make it possible to achieve improved compound processing characteristics, while also providing improved flexibility and durability in the end-use product. A plasticizer is generally an organic molecule having 100-1000 g/mole in molecular weight. Standard or conventional plasticizers generally include phthalate and terephthalate-based plasticizers.

The terms "plasticizer efficiency" or "plasticizing efficiency" as used herein, refers to the ability of a plasticizer to make a polymer product softer and is reported as a ratio of the slope of the hardness versus plasticizer concentration to the slope of that found for dioctyl phthalate (DOP) in the polymer product.

The terms "a derivative of 2,4-FDCA" as used herein, refers to a diester of 2,4-FDCA selected from the group consisting of dimethyl 2,4-furandicarboxylic acid (2,4-DMFDCA), diethyl 2,4-furandicarboxylic acid, and combination thereof.

The term "suitable additive" as used herein, refers to any one or more additives typically used in polymer industry, such as a light stabilizer, an acid stabilizer, a thermal stabilizer, a UV stabilizer, an antioxidant (AO), an antistatic agent, a filler, a reinforcement, a biocide, an expansion agent, a demoulding additive, a lubricant, a flow modifier, an impact modifier, an antiblocking agent, a slipping agent, a pigment, a flame retardant, an additional plasticizer other than the dialkyl esters of 2,4-FDCA, and combinations thereof. The additional plasticizer includes but not limited to $C_4$-$C_{13}$ dialkyl phthalates, alkyl benzoates, trialkyl trimellitates, dialkyl adipates, alkyl 1,2-cyclohexanedicarboxyates, alkyl 1,3-cyclohexanedicarboxyates, alkyl 1,4-cyclohexanedicarboxyates, glyceryl esters, isosorbide ester, epoxidized vegetable oils, fully or partially epoxidized saturated and unsaturated fatty acid esters, citric triesters, alkylpyrrolidones, or combinations thereof.

In the context of the sustainable development of new plasticizers, 2,5-furandicarboxylic acid (2,5-FDCA) derivatives appear as renewable building blocks with the potential to bring a new dimension of competition to terephthalates. One of the main appeals of this platform is that these acids can be produced from sugar, by fermentative routes. For example, WO 2012/113609, WO 2012/11360, DE 102009028975A1, WO 2011/023491 and U.S. Pat. No. 9,175,148 generally describe the application of diesters of 2,5-FDCA presenting lateral alkyl $C_5$, $C_7$, $C_9$, $C_{10}$ and $C_{11}$-$C_{13}$ (respectively) as plasticizers for PVC in formulation ranges from 5 to 200 phr (parts per hundred parts of PVC resin). These furanic plasticizers exhibit phthalate-like performance with regard to compatibility and migration. Similar results are found in *Polym. Chem.*, 2019, 10, 5324-5332 and *Journal of Polymer Science, Part A: Polymer Chemistry* 54, 11-332016. In terms of toxicity, a property that has been driving the adoption of non-phthalate solutions, Matos et al. generally describes in the publication *Materials* 2019, 12, 2336 that the 2,5-FDCA-based plasticizer diethylhexyl furanoate (also known as 2,5-DEHF) has its metabolites exhibiting similar terephthalate toxicity. In terms of using other isomers of FDCA, U.S. Pat. No. 10,294,347 teaches the production of 2,5- and 2,3-FDCA dialkyl esters and their use as $C_4$ to $C_{22}$ plasticizers in PVC. However, to date, none of these diesters have matured enough to show commercialization promise in the near future.

Disclosed herein is a new and preferably renewable plasticizer for polymers including PVC which provide the polymers improved or at least equal properties such as flexibility, durability, processability and safety, as compared to the current existing plasticizers including phthalate-derived plasticizers, terephthalate-derived plasticizers and plasticizers derived from 2,5-FDCA diesters. The new plasticizers and the processes of making the new plasticizers of the present disclosure described herein may be able to circumvent a barrier faced by plasticizer producers in the furanic area, facilitating the production of affordable furanic diesters of 2,4-FDCA. Surprisingly, PVC compositions plasticized with these 2,4-FDCA diesters exhibited lower Shore A hardness at the same plasticizer concentration as compared to that of the currently existing plasticizers in the PVC compositions, as shown in FIG. 1 of the present disclosure. The experimental results demonstrated that some of the 2,4-FDCA diesters developed according to the present disclosure have higher plasticizing efficiency than the currently existing plasticizers. Surprisingly, these 2,4-FDCA diesters also exhibited lower migration and more advantageous safety than currently existing plasticisers in polymer compositions.

Described herein are new plasticizers based on 2,4-isomer of furandicarboxylic acid diesters of the present disclosure which may be used in polymer materials including PVC. These plasticizers may overcome one or more of the above mentioned disadvantages of existing plasticizers or at least provide a useful alternative. Also described is a cost effective process of preparing the plasticizer based on 2,4-isomer of furandicarboxylic acid diesters. This process may be cost effective as compared to that of the existing plasticizers. Also disclosed is a composition comprising the plasticizer based on 2,4-isomer of furandicarboxylic acid diesters, as well as a method of preparing such composition. Also disclosed is a polymer material comprising the plasticizer based on 2,4-isomer of furandicarboxylic acid diesters with improved or at least equal flexibility, durability, processability and safety as compared to the same material plasticized with the current existing plasticizers.

In one aspect of the present disclosure, an innovative non-phthalate compound of dialkyl ester of 2,4-furandicarboxylic acid having the chemical structure of Formula is disclosed:

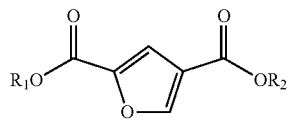

$R_1$ and $R_2$=alkyl radical deriving from $C_4$-$C_{13}$ monohydric aliphatic primary alcohols Formula I. Chemical structure of dialkyl ester of 2,4-furandicarboxylic acid of the present disclosure.

wherein $R_1$ and $R_2$ each represent an alkyl radical of a $C_4$-$C_{13}$ monohydric aliphatic primary alcohol including, but not limited to, 2-ethylhexanol, ethylhexanol, n-butanol, isononyl alcohol, isobutanol, isodecyl alcohol, 2-methyl-1-pentanol, 2-propylheptanol, $C_6$-$C_{11}$ linear alcohols, tridecyl alcohol, isooctyl alcohol, amyl alcohol and other structural isomers of the alcohols with the general structure described above.

In one embodiment, $R_1$ and $R_2$ are two different alkyl radicals. In another embodiment, $R_1$ and $R_2$ are preferably the same alkyl radical. In yet another embodiment, $R_1$ is a linear alkyl radical. In yet another embodiment, $R_1$ is a branched alkyl radical. In yet another embodiment, $R_2$ is a linear alkyl radical. In yet another embodiment, $R_2$ is a branched alkyl radical. In yet another embodiment, each of R1 and R2 is an alkyl radical derived from ethylhexanol and the resulting compound is di (ethylhexyl)-2,4-furanoate In another aspect of the present disclosure, a process of preparing an innovative non-phthalate compound of dialkyl ester of 2,4-furandicarboxylic acid having the chemical structure of Formula I shown above is also described. The process comprises synthesizing 2,4-furandicarboxylic acid (2,4-FDCA) or a derivative of 2,4-FDCA; and esterifying the 2,4-FDCA or the derivative of 2,4-FDCA with an alcohol to obtain a dialkyl ester of 2,4-furandicarboxylic acid having the chemical structure of Formula I discussed above, wherein $R_1$ and $R_2$ each represent an alkyl radical deriving from a $C_4$-$C_{13}$ monohydric aliphatic primary alcohols including, but not limited to, 2-ethylhexanol, n-butanol, isononyl alcohol, isobutanol, isodecyl alcohol, 2-methyl-1-pentanol, 2-propylheptanol, $C_6$-$C_{11}$ linear alcohols, tridecyl alcohol, isooctyl alcohol, amyl alcohol and other structural isomers of the alcohols with the general structure described above. In one embodiment, $R_1$ and $R_2$ are the same alkyl radical. In another embodiment, $R_1$ and $R_2$ are two different alkyl radicals. The 2,4-furandicarboxylic acid diesters resulting from this process can have their properties tuned according to variations in the length and structure of the alkyl chain lengths deriving from the alcohol.

In another embodiment, the new furan isomer, the 2,4-furandicarboxylic acid (2,4-FDCA) is synthesized from renewable sources through fermentative processes with intrinsically low environmental impact. Moreover, the process is able to bring the production costs of this new isomer to levels compatible with those of terephthalic acid and phthalic anhydride. In another embodiment, 2,4-FDCA is produced via catalytic routes comprising several synthetic steps as described in *Org. Proc. Res. Dev.* 2003, 7, 1, 74-81, *Anti-Infective Agents*, 2012, 10, 55-71 and *ACS Sustainable Chem. Eng.* 2016, 4, 3, 1707-1714. The esterification to yield the final diester can be adapted from the methodologies discussed in *Materials* 2019, 12, 2336, where a furanic diacid (in this case, 2,5-FDCA) can react with an excess of 2-ethyl-hexanol in the presence of sulfuric acid (1 wt. %) at 160° C. for 6 hours. This step can be reproduced with either bio-based or oil-based 2,4-FDCA.

In another embodiment, the compound of dialkyl ester of 2,4-furandicarboxylic acid comprises isomeric $C_4$-$C_{13}$ dialkyl furandicarboxylates, with isomeric $C_4$-$C_{13}$ dialkyl groups selected from unbranched, singly, doubly, triply and quadruply branched alkyl chains, and a mixture thereof.

In another embodiment, the 2,4-furandicarboxylic acid (2,4-FDCA) or its derivative is synthesized from a renewable material, e.g. sugars to produce bio-based 2,4-FDCA that permits the compound dialkyl ester of 2,4-furandicarboxylic acid to contain different levels of bio-based carbon, as typically tested and measured according to ASTM D6866.

In another embodiment, the plasticizer exhibits a bio-based carbon content. As mentioned above, the total bio-based or renewable carbon in the plasticizer may be contributed from the bio-based furan dicarbolylic acid and/or the plasticizing alcohols, depending on the sources of both components. ASTM D6866 distinguishes carbon resulting from contemporary biomass-based inputs from those derived from fossil-based inputs. Biomass contains a well-characterized amount of Carbon-14 that is easily differentiated from other materials such as fossil fuels that do not contain any Carbon-14. Since the amount of Carbon-14 in biomass is known, a percentage of carbon from renewable sources can be calculated easily from the total organic carbon in the sample.

In another embodiment, the compound exhibits a bio-based carbon content as determined by ASTM D6866, ranging from about 0.1% to about 99%, from about 0.1% to about 90%, from about 0.1% to about 75%, or preferably from about 29% to more than 90%.

In another embodiment, the 2,4-FDCA is produced by a recombinant microorganism capable of producing 2,4-FDCA from a feedstock comprising a carbon source comprising of a hexose, a pentose, glycerol, $CO_2$, sucroses and/or combinations thereof, for example, as described in U.S. patent application Ser. No. 16/806,728 (not public yet). The entire contents of U.S. patent application Ser. No. 16/806,728 are incorporated herein by reference.

In another embodiment, the 2,4-FDCA is obtained from renewable sources and catalytic pathways, such as the routes described in U.S. Pat. No. 9,284,290, Green Chem., 2014, 16, 1957-1966, *ACS Sustainable Chem. Eng.* 2016, 4, 3, 1707-1714 and U.S. Pat. No. 8,455,668. The entire contents of U.S. Pat. No. 9,284,290 is incorporated herein by reference. The method for synthesizing 2,4-FDCA by a disproportionation route comprises the following steps: a) oxidizing furfural compounds in the presence of catalysts and alkaline solution in order to obtain bio-based furoic acid salts, wherein the catalysts are selected from the group consisting of Au/$TiO_2$, Au/C, Au/ZnO, Au/$Fe_2O_3$ or other Au catalysts; b) heating the furoic acid salts under stirring in the presence of a metal based catalyst to prepare a reaction mixture and cooling the reaction mixture until room temperature; c) collecting furan from the reaction mixture obtained in item b) in order to obtain the mixture of 2,4-FDCA and 2,5-FDCA; and d) subjecting the mixture obtained in item c) to an extraction or other separation method in order to collect and purify 2,4-FDCA.

In another embodiment, the 2,4-FDCA or its derivative is obtained from renewable sources and catalytic pathways, e.g., those described in *ACS Sustainable Chem. Eng.* 2016, 4, 3, 1707-1714 and U.S. Pat. No. 8,455,668. The entire contents of U.S. Pat. No. 8,455,668 is incorporated herein by reference. Starting from glycerol derivatives, glyceraldehyde or dihydroxyacetone, 5-HMF, or 4-HMF could be obtained through base-catalyzed condensation and acid-catalyzed dehydration steps in the batch process. 4-HMF oxidation would lead to 2,4-FDCA.

In another embodiment, the process of preparing the compound of dialkyl ester of 2,4-FDCA comprises using a stoichiometric excess (5 to 100% by mole) of the plasticizing alcohol to react with 2,4-FDCA or a suitable derivative of 2,4-FDCA, optionally in the presence of a esterification catalyst such as Bronsted and Lewis acids, organic and inorganic acids, or metal catalysts such as tin (II) derivatives and metal esters such as titanium and zirconium esters and metal alkoxides such as antimony oxides and zeolites. In another embodiment, the process of preparing the dialkyl ester of 2,4-FDCA further comprises removing the excess of alcohol by vacuum evaporation after the complete conversion of the 2,4-FDCA or a suitable derivative of 2,4-FDCA into a dialkyl ester of 2,4-FDCA.

In another embodiment, the process of preparing the compound of dialkyl ester of 2,4-FDCA further comprises dissolving the obtained compound in dichloromethane to form a solution; treating the solution with an activated charcoal to absorb impurities such as titanium catalyst to the charcoal; filtering the treated solution to remove the charcoal and the impurities absorbed to the charcoal; and evaporating the dichloromethane under vacuum.

Another aspect of the present disclosure provides a composition comprising a polymer and the compound of dialkyl ester of 2,4-FDCA discussed above as a plasticizer in an amount of 1 to 300, more preferably 10 to 150, even more preferably 15 to 80 parts per weight of the compound per 100 parts per weight of polymer.

In one embodiment, the polymer is polyvinyl chloride (PVC).

In another embodiment, the polymer is selected from the group consisting of PVC, polyvinyl butyral (PVB), thermoplastic polyurethane (PU), polylactic acid (PLA), polyhydroxybutyral (PHB), polybutylene succinates (PBS), polybutylene succinate adipates (PBSA), polyethers, polysulfides, polysuldones homo- and copolymers of polystyrene (PS), polycarbonates (PC), polyalkyl methacrylates (PAMA), starch, thermoplastic starch (TPS) and combinations thereof.

In another embodiment, the PVC is derived from suspension, bulk solution, emulsion or microsuspension polymerization processes.

In another embodiment, the dialkyl ester of 2,4-FDCA compound is present in the composition in an amount of 1 to 300, more preferably 10 to 150, even more preferably 15 to 80 parts per weight of the compound per 100 parts per weight of polymer.

In another embodiment, the composition further comprises one or more suitable additives typically used in polymer compositions such as light, acid, thermal and UV stabilizers, fillers and reinforcements, biocides, expansion agents, demoulding additives, lubricants, flow modifiers, impact modifiers, antiblocking agents, antistatic agents, slipping agents, pigments and flame retardants.

In another embodiment, the composition further comprises an additional plasticizer selected from the group consisting of $C_4$-$C_{13}$ dialkyl phthalates, alkyl benzoates, trialkyl trimellitates, dialkyl alkyl 1,2-cyclohexanedicarboxyates, alkyl 1,3-adipates, cyclohexanedicarboxyates, alkyl 1,4-cyclohexanedicarboxyates, glyceryl esters, isosorbide ester, epoxidized vegetable oils, saturated and unsaturated fatty acid esters which may be fully or partially epoxidized, citric triesters, alkylpyrrolidones, and combinations thereof.

In another embodiment, the additional plasticizer is preferably a non-phthalate diester (also referred as ortho-plasticizers).

Another aspect of the present disclosure provides a method of preparing a composition comprising a polymer and the compound of the dialkyl ester of 2,4-FDCA discussed above as a plasticizer, wherein the method comprises mixing the polymer in a powder or pallet form, the dialkyl ester of 2,4-FDCA and other additives such as Ca/Zn stabilizer and stearic acid together to form a dry blend; filling the dry blend into a two roll mill; and processing the mill for more than three minutes to facilitate the plasticizer incorporation and the homogenization of the composition.

In yet another aspect, the present disclosure provides a polymer product comprising a composition comprising a polymer and the compound of the dialkyl ester of 2,4-FDCA discussed above as a plasticizer.

In one embodiment, the polymer product is selected from the group consisting of paints, inks, adhesives or adhesive components, sealing compounds, coating compositions, lacquers, plastisols, synthetic leather, solvents, lubricating oil, floor coverings, underbody protection, fabric coatings, cables or wire insulation, extruded articles, and films. The polymer product is produced by traditional means such as calendering, extrusion, or any other technique able to melt and mix effectively the additive in the composition.

Yet another aspect of the present disclosure provides a method of making a polymer product comprising a composition comprising a polymer and the compound of the dialkyl ester of 2,4-FDCA as a plasticizer as discussed above the first, the polymer in a powder or pallet/granule form, the dialkyl ester of 2,4-FDCA and other additives such as Ca/Zn stabilizer and stearic acid may be mixed together to form a dry blend. The dry blend may be input to a mill, e.g., a two roll mill. The dry blend is processed in the mill, e.g., to facilitate the plasticizer incorporation and homogenization of the composition, e.g., for three minutes. The resulted homogenized composition may be processed into the polymer product by calendering, extrusion, injection moulding or any other processing technique suitable to transform the polymer composition into the polymer product.

An advantage of the present disclosure is that the compound of the dialkyl ester of 2,4-FDCA as a plasticizer can have higher plasticizing efficiency than phthalate-derived plasticizers, and lower migration/exudation than aliphatic plasticizers such as those from modified triglycerides. Therefore, a polymer product, such as PVC product, plasticized with the compound of the dialkyl ester of 2,4-FDCA exhibits longer shelflives, lower additivation requirements during compounding, lower values of hardness and more reliable and durable performance over the course of time.

Another advantage of the present disclosure is that the compound of the dialkyl ester of 2,4-FDCA (2,4-DEHF) can have lower volatility. Based on structural parameters such as reduced symmetry and a dipolar moment deriving from the presence of an heteroatom in the central molecular segment, it is anticipated that 2,4-DEHF as a plasticizer in a PVC composition show lower relative mobility in the PVC composition than phthalates and terephthalate-based plasticizers.

Another advantage of the present disclosure is that the dialkyl ester of 2,4-FDCA (2,4-DEHF) in a PVC composition can show lower relative mobility in the PVC composition than aliphatic plasticizer, such as adipates, vegetable oils and their derivatives such as epoxidized vegetable oils and esters thereof.

This advantage can be further magnified through the production of the branched dialkyl esters of 2,4-FDCA. As a result, compositions prepared with the branched dialkyl esters of 2,4-FDCA as a plasticizer can show reduced loss of the plasticizer as a result of exudation or vaporization. This characteristic can be also translated in a more reliable processing since one skill in the art can have more control over the amount used during the preparation of the composition and more reliable control of properties over time. In this regard, 2,4-FDCA diesters can be incorporated into PVC resins to produce compositions by traditional means such as calendering, extrusion, injection moulding or any other technique able to melt and mix effectively the additive in the formulation.

EXAMPLES

The present disclosure is further illustrated by the following non-limiting examples.

Example 1

The in vivo production of 2,4-FDCA by a recombinant microorganism as described in U.S. patent application Ser. No. 16/806,728 from glucose was evaluated in shake flask fermentations in triplicate, using a defined media comprising about 2.2 g/L $KH_2PO_4$, 9.4 g/L $K_2HPO_4$, 1.3 g/L $(NH_4)_2SO_4$, 10 mg/L thiamine, 320 mg/L EDTA-NaOH, 2 mg/L $CoCl_2 \cdot 6H_2O$, 10 mg/L $MnSO_4 \cdot H_2O$, 5 mg/L $CuSO_4 \cdot 5H_2O$, 2 mg/L $H_3BO_3$, 2 mg/L $Na_2MoO_4 \cdot 2H_2O$, 54 mg/L $ZnSO_4 \cdot 7H_2O$, 1 mg/L $NiSO_4 \cdot 6H_2O$, 100 mg/L citrate Fe (III), 100 mg/L $CaCl_2) \cdot 2H_2O$, 0.3 g/L $MgSO_4 \cdot H_2O$. Carbon source was provided by 10 g/L glucose and nitrogen sulphate was used as nitrogen source for the production of 2,4-FDCA. Erlenmeyer flasks were inoculated with the recombinant strain to an initial optical density (OD600) of 0.1, and incubated at 37° C., 225 rpm for about 48 hours. Analysis of supernatant in 48 hours by high-performance liquid chromatography (HPLC) indicated the production of 14±2 mg/L 2,4-FDCA. The term "EDTA-NaOH" as used herein, refers to the soluble salt of ethylenediaminetetraacetic acid (EDTA) and sodium hydroxide (NaOH).

Example 2

A study investigated a non-limiting example of a procedure of preparing the 2,4-FDCA as the plasticizer of the present disclosure.

In this non-limiting example, the procedure for synthesizing 2,4-FDCA by a disproportionation route comprises the following steps: a) oxidizing furfural compounds in the presence of catalysts and alkaline solution in order to obtain bio-based furoic acid salts, wherein the catalysts are selected from the group consisting of $Au/TiO_2$, Au/C, Au/ZnO, $Au/Fe_2O_3$ or other Au catalysts; b) heating the furoic acid salts under stirring in the presence of a metal based catalyst to prepare a reaction mixture and cooling the reaction mixture until room temperature; c) collecting furan from the reaction mixture obtained in item b) in order to obtain the mixture of 2,4-FDCA and 2,5-FDCA; and d) subjecting the mixture obtained in item c) to an extraction or other separation method in order to collect and purify 2,4-FDCA. The procedure is described in more details below.

Procedure for Preparing Furoic Acid from Furfural: Oxidation of Furfural

Furfural (3.00 grams, 31.22 mmol) was dissolved in 40 ml water. One equivalent (31.75 mmol; 1.02 eq) of base (NaOH) and 0.012 grams of Au/TiO$_2$ catalyst (ex-Strem-Autek; 1.2 wt. % Au, Au particle size 2-3 nm) were added to the furfural solution in water. The 100 ml reaction vessel (Büchi glasuster picoclave) was closed and overhead stirring was applied. Oxygen pressure (303974.99 Pa of O$_2$) was applied to the reaction mixture. The reaction mixture was put at 50° C. After one hour reaction the pressure has dropped to approximately one atmosphere and the reaction vessel was re-pressurised to 303974.99 Pa of O$_2$ and subsequently stirred overnight. After overnight stirring the reaction was stopped and the catalyst was filtered off. The solvent (water) was removed by a rotary evaporator and applying vacuum. The yield of sodium furoate was 94.9%.

The use of gold catalysts in the above reaction often is a little bit more selective than other metal based catalysts such as Pt or Pd and under the circumstances used in the reaction, the combination of a heterogeneous catalyst that acts under the same basic conditions required for the subsequent disproportionation reaction is advantageous.

This reaction demonstrates the efficiency in obtaining furoate salts from furfural, that can serve as input for the subsequent disproportionation reaction.

Process for Production of a Mixture of 2,4-FDCA and 2,5-FDCA 6.00 grams of K-furoate (39.95 mmol) and 2.20 grams of CdI$_2$ (6.01 mmoles) were grinded together well and charged into a 3-necked flat flange reaction vessel. The mixture was then heated in a salt bath at 265° C. with stirring using a mechanical overhead stirrer under continuous (very slow) flow of nitrogen. During the course of reaction, the furan formed was collected via a Dean-Stark trap and an CO$_2$/Acetone ice bath (–78° C.), yielding furan of 1.35 grams (95% of the theoretical amount). After 4 hours, the reaction was stopped and allowed to cool down at room temperature for 1 h. Thus obtained black hard solid substance was dissolved in water (50 mL). A residual amount of water insoluble black material was filtered off and the deep yellow colour filtrate was acidified using 12 N HCl (until pH: 1). 2,5-FDCA was precipitated and filtered off. 60.9% of the theoretical amount of 2,5-FDCA was isolated. NMR analysis of the reaction mixture after filtering off the insoluble black material showed that the K-furoate had been converted over 90% and that there is a mixture being present of 2,4-FDCA and 2,5-FDCA, in a ratio of 0.32:0.68. Based upon this and the 60.9% of 2,5-FDCA isolated, it can be calculated that the K-furoate has been disproportionated into a mixture of furandicarboxylic acids in 89% of the theoretical yield.

Procedure for Purification of 2,4-Furandicarboxylic Acid (2,4-FDCA)

The reaction crude mixture (2,4-FDCA, 2,5-FDCA, 2-Furoic acid and CdI$_2$) was subjected to soxhlet extraction using acetone for 8 h. After cooling to room temperature, acetone insoluble white crystalline powder was analyzed by NMR which showed no proton signals. The acetone soluble part was recovered and the solvent was evaporated under reduced pressure in the rotatory evaporator. The NMR analysis showed the presence of 2,4-FDCA, 2,5-FDCA and 2-Furoic acid in the crude mixture. The mixture was then stirred vigorously with chloroform for 10 min at room temperature and filtered. This process was repeated until 2-furoic acid was completely removed from the mixture. The product was then dried in a vacuum oven at 40° C. for 12 h. As the solubility difference of 2,4-FDCA was comparatively high in acetone at room temperature, the same technique (adapted with chloroform previously) was repeated with acetone to separate the 2,4-FDCA from 2,5-FDCA. Thus acetone soluble part was separated, combined together and evaporated under reduced pressure in a rotatory evaporator yielded 2,4-FDCA, which was not 100% qualitative, but not less than 85% purity and the investigation is in progress to find the more precise way to get 100% pure compound of 2,4-FDCA.

The use of the process described herein allows 2,4-FDCA yields of at least 7 wt. %, preferably at least 15 to 20 wt. %, more preferably 32 wt. % at least (the remaining fraction of the products is basically 2,5-FDCA). The 2,4-FDCA is produced from cheap and renewable stock feeds, e.g. furfural, through a simple 2-step process which produces no harmful, toxic or undesirable by-products (the main by-product furan has actually highly interesting applications).

Example 3

A study investigated a non-limiting example of a procedure of preparing 2,4-FDCA for the plasticizer of the present disclosure.

In a 250 mL jacketed glass reactor, dihydroxyacetone (10.0 g, 0.11 mol, 1 eq) was dissolved in deionized water (100 mL). The solution was cooled down to 0° C., and Ambersep-900 basic ion exchange resin (27.8 g) was added. The mixture was then stirred at 0° C. for 24 h. After filtration to remove the resin, the product was freeze-dried.

In a 100 mL round-bottom flask, the product was redissolved in DMSO (50 mL), to which was added Amberlyst-15 acidic ion exchange resin (5.0 g). The set-up was equipped with a Dean-Stark apparatus for collecting the water generated during the dehydration. The mixture was stirred at 110° C. for 5 h and then cooled down to room temperature and filtered. The filtrate was concentrated under vacuum to remove most DMSO, keeping the temperature below 50° C. Next, the product was extracted by a dichloromethane/NaHCO$_3$(1M) separation. The organic layer was dried over anhydrous sodium sulfate and the solvent was evaporated under reduced pressure. The final product (mixture of 4- and 5-HMF) was obtained as a brown viscous.

In a 250 mL round-bottom flask, 4-HMF was dissolved in a sodium hydroxide aqueous solution (9.2 g NaOH in 100 mL of deionized water). The mixture was cooled down to 0° C., and potassium permanganate (3.4 g, 22 mmol, 34 eq) was added. Then, the solution was stirred at 0° C. for 15 min. The precipitate of manganese oxide was filtered off, and a concentrated HCl solution was carefully added to the filtration to bring the pH into 1, while keeping the temperature below 5° C. The resulting mixture was extracted with diethyl ether (×2). The organic layer was dried over anhydrous sodium sulfate and concentrated in vacuo. The product was obtained as a yellow powder.

Example 4

A study investigated the processes of synthesizing the compound of dialkyl ester of 2,4-furandicarboxylic acid of the present disclosure.

The novel dialkyl diester based on the 2,4-FDCA moiety is prepared via the esterification of the methyl-furanoate with 2-ethyl-hexanol in the presence of Ti catalyst, as described in Scheme 1 below. Dimethyl 2,4-furandicarboxylic acid (2,4-DMFDCA) (4.4 g, 23.9 mmol, 1 eq) and 2-ethyl-1-hexanol (9.34 g, 71.7 mmol, 3 eq) were charged into a 10 mL round-bottom flask. The set-up was purged with argon gas. Then, the reaction mixture was heated at 115° C. for 15 min with constant stirring. After observing the complete melt of the mixture, the catalyst Ti (OiPr)$_4$ (0.34 g, 1.2 mmol) in 2.9 mL of toluene was added into the flask under a continuous flow of argon gas. The temperature was increased to 140° C. and stirred for 3 h. The excess of 2-ethyl-1-hexanol was removed by vacuum evaporation. Then, the obtained crude product was dissolved in 20 mL of dichloromethane and treated by activated charcoal for eliminating the titanium catalyst and discoloring the product. After filtration of the charcoal and evaporation of dichloromethane under vacuum, the final product was obtained as an amber oil with a yield of 82% (7.5 g) and a purity of 98.0 wt. % (1H NMR titration).

The synthetic protocol and the success of the synthesis was confirmed by FTIR (Fourier Transformation Infrared) spectroscopy and 1H NMR (1H Nuclear Magnetic Resonance). FTIR confirmed the success of the reaction through a detailed analysis of the signals of the region related to the carbonyl stretch (—C=O) (1500-1750 cm$^{-1}$), which have shifted to values characteristic of resulting ester. Other signals referring to (C—C—O—) and (O—C—C) stretching and also characteristic of the ester product were found at 1240 and 1050 cm$^{-1}$, respectively. Moreover, 1H NMR confirmed the formation of the targeted dialkyl ester through the presence of characteristic signals in 4.2 ppm that confirmed the attachment of the alkyl residue in the furanic moiety. Traces of residual alcohol were found neither in the FTIR nor in the 1H NMR analysis.

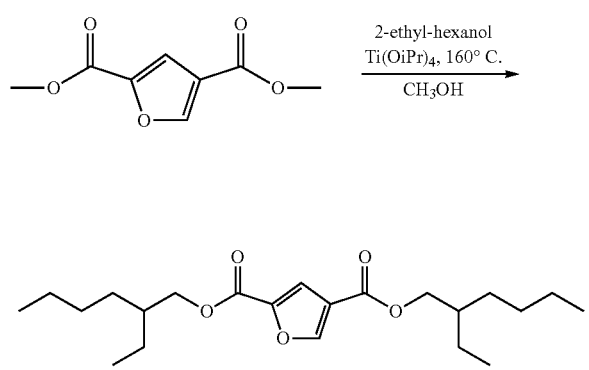

Scheme 1. Scheme of preparation of a dialkyl ester of 2,4-FDCA, specifically diethylhexyl 2,4-furanoate (2,4-DEHF), by reacting 2,4-DMFDCA with 2-ethyl-hexanol Complementary properties such as the thermal stability of the resulted dialkyl ester of 2,4-FDCA are investigated by thermogravimetric analysis (TGA) and dynamic scanning calorimetry (DSC). This characteristic can be compared against the processing window typically used for PVC to demonstrate the applicability of such plasticizers and to be used to benchmark this novel molecule against commercial plasticizers in terms of stability.

The thermogravimetric analysis (TGA) has been conducted. The TGA analysis and the test results are detailed in Example 6 and FIG. 2 below.

The same synthetic protocol could be replicated starting from 2,4-FDCA in the diacid form, with the only difference being the condensation of water instead of methanol during the reaction phase, and from 2,4-FDCA and its derivatives from both fossil and bio-based sources. Moreover, the synthetic protocol can accommodate alcohols with different chain lengths (ranging from $C_4$ to $C_{13}$), such as 1-butanol, 2-butanol, isobutanol, pentanol, hexanol, heptanol, octanol, 1-nonanol, isononanol, decanol, undecanol, dodecanol, tridecanol and mono-, bi-, tri and quadribranched structural isomers thereof, as well as mixtures of the alcohols described.

Example 5

A study investigated the process of preparing dry blends of a polymer composition comprising PVC and the plasticizer of dialkyl ester of 2,4-FDCA of the present disclosure.

On a later stage, a dialkyl ester of 2,4-FDCA, specifically the diethylhexyl 2,4-furanoate (2,4-DEHF), was prepared and used as a plasticizer to produce a flexible PVC composition to demonstrate the advantageous properties associated with the use of 2,4-DEHF in terms of processability and final performance. For that purpose, dry blends were produced by adding in a beaker of suitable volume a specific amount of the novel 2,4-DEHF plasticizer of the present disclosure into the PVC resin powder (Braskem Norvic SP 700RA, nominal K value 57) together with additives such as Ca/Zn stabilizer and stearic acid. Components were thoroughly mixed with a spatula to form a dry blends. The dry blends were manually fed into a Mecanoplast two roll mill and processed over three minutes with manual mixing to enhance homogenization and facilitate the plasticizer incorporation. Any other time adequate to result in plasticization the mixture, as tracked by the gelation behavior, can be used to produce the flexible PVC compounds with 2,4-DEHF. Test samples of the present disclosure were prepared by calendering, but any other processing technique suitable to transform PVC whilst simultaneously incorporate the plasticizer in the compound can be used. When calendering, the rolls were heated to 110 and 140° C. respectively, but conditions can be adjusted to any other temperature and roll speed suitable to soften the PVC and enable processing/mixing effectively.

The PVC compositions were specifically produced herein with 40 phr (parts per hundred parts of PVC resin) of plasticizer as a matter of example, but contents from 1 to 300 phr of plasticizer are suitable based on the expected relative lower migration of this 2,4-furanoate diesters in comparison with commercial counterparts. Apart from 2,4-DEHF plasticizer, phthalate and non-phthalate control plasticizers were used for the preparation of comparative control samples through the same methodology described above. Samples of DOTP from two suppliers were tested, hence DOTP_1 and DOTP_2.

The compositions of the test samples of the present disclosure and the comparative control samples are described in Table 1 below.

TABLE 1

Dry Blend Compositions: Example of Inventive Formulation and Comparative Examples.

| Dry Blend | 1* | 2 | 3 | 4 | 5 | 6 | 7 | 8 | 9 |
|---|---|---|---|---|---|---|---|---|---|
| PVC Norvic SP 700RA | 100 | 100 | 100 | 100 | 100 | 100 | 100 | 100 | 100 |
| DEHF | 40 | | | | | | | | |
| DOTP_1 | | 40 | | | | | | | |
| DOTP_2 | | | 40 | | | | | | |
| DOP | | | | 40 | | | | | |
| DOA | | | | | 40 | | | | |
| DINP | | | | | | 40 | | | |
| INBRAFLEX 5.0 | | | | | | | 40 | | |
| INBRAFLEX 3.4 | | | | | | | | 40 | |
| DRAPEX 6.8 | | | | | | | | | 40 |
| Ca/Zn Stabilizer | 2 | 2 | 2 | 2 | 2 | 2 | 2 | 2 | 2 |
| Stearic acid | 0.2 | 0.2 | 0.2 | 0.2 | 0.2 | 0.2 | 0.2 | 0.2 | 0.2 |

*Test Samples of the Present disclosure (Inventive Formulation)

The chemical name of the plasticizers listed in Table 1 above are detailed in the following:

DEHF (the plasticizer of the present disclosure)—Diethylhexyl 2,4-Furanoate (2,4-DEHF) (or Bis (2-Ethylhexyl) 2,4-Furanoate, which is one example of the dialkyl ester of 2,4-FDCA of the present disclosure;

DOPT—Diethylhexyl terephthalate (or Bis (2-Ethylhexyl) Terephthalate)—the denomination 1 and 2 used after DOPT in Table 1 refers to different suppliers;

DOP—Diethylhexyl Phthalate (or Bis (2-Ethylhexyl) Phthalate);

DOA—Dioctyl Adipate;

DINP—Diisononyl Phthalate;

INBRAFLEX 5.0—Commercial formulation of non-specified ester of epoxidized soybean oil;

INBRAFLEX 3.8—Commercial formulation of non-specified epoxidized soybean oil; and DRAPEX 6.8—commercial formulation of epoxidized soybean oil Example 6

A study investigated the thermal properties of the PVC compositions plasticized with 2,4-DEHF.

Thermal performance of the PVC compositions plasticized with the dialkyl esters of 2,4-FDCA of the present disclosure was determined by TGA (thermogravimetric analysis). The tests were run using approximately 10 mg of the compound sample, from room temperature to 1000° C., under $N_2$ atmosphere, heating rate of 10° C./min. The resulted thermogravimetric curves of the test samples of a compound with the dialkyl esters of 2,4-FDCA of the present disclosure as a plasticizer versus comparative control samples with standard phthalate and terephthalate-based plasticizer DOP are shown in FIG. 2.

Figure 2:
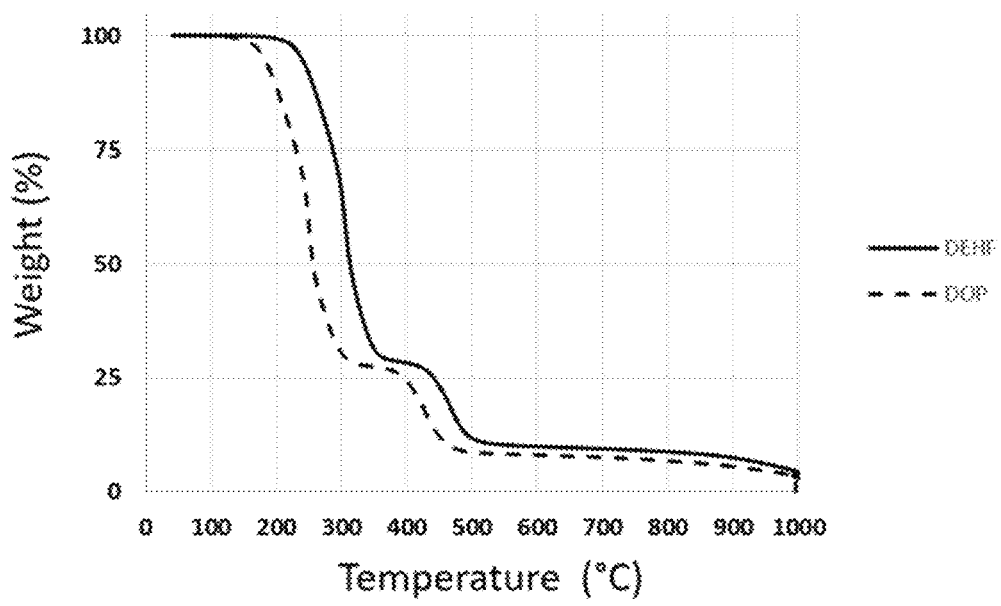
FIG. 2 shows the thermogravimetric curve of the test samples of a compound with the dialkyl esters of 2,4-FDCA of the present disclosure as a plasticizer versus comparative control samples with standard phthalate and terephthalate-based plasticizers.

FIG. 2 compares the thermal stability of compounds prepared with the inventive dialkyl ester with a comparative sample prepared with commercially available DOP. The test results in FIG. 2 demonstrated that the resulting compound prepared with the inventive plasticizer (the dialkyl esters of 2,4-FDCA) had superior thermal stability as compared to the compound prepared with standard phthalate and terephthalate-based plasticizer.

Example 7

A Study Investigated the Plasticizing Efficiency of the Plasticizers of the Present Disclosure Using Shore a Hardness The Shore A hardness test probes the softness of a given PVC composition by correlating how deep a standardized needle penetrates the sample with a hardness scale. In this regard, the plasticizing efficiency of the plasticizer can be understood as the capacity of the plasticizer to soften the PVC resin. Therefore, the lower the hardness value, the greater the plasticizing efficiency of a given plasticizer. This is a very important aspect in the PVC sector since the hardness value is used to characterize certain grades, and formulations adjustments are typically designed aiming at a target Shore A value range.

The Shore A hardness of the PVC composition plasticized with different plasticizers were determined according to ASTM D2240 standard and the test results are shown in FIG. 1. As shown in FIG. 1, the test samples of the PVC composition plasticized with 2,4-DEHF of the present disclosure showed lower Shore A hardness values than those observed for phthalates and terephthalate-based counterparts. The experimental results clearly demonstrated that the novel 2,4-DEHF plasticizer exhibits greater plasticizing efficiency in the PVC composition than that of the standard phthalates and terephthalate-based plasticizers in the PVC compositions. Therefore, it is possible to reduce the plasticizer content to achieve a given PVC composition with a target hardness value by using the diesters of the present disclosure described herein, as compared to the phthalate or terephthalate-based plasticizer.

Example 8

A study investigated the permanency of the plasticizers of the present disclosure in the PVC compositions, which may be important in many application.

Permanency is linked with the resistance of a given plasticizing molecule (or any other additive) to exudate from the PVC compositions to food, packaging surface, or any other item in contact with the PVC composition. Apart from problems related to contamination and to the exposure of users to hazardous substances, which is a problem particularly associated with phthalates, this phenomenon also is responsible for negative changes in performance over the course of time.

Migration tests were conducted in an oven to simulate and accelerate the potential exudation phenomenon according to standard ANBT-NBR NM-IEC 60811-3-2. Samples of the inventive compound 1 and the comparative example 4 (shown in Table 1) were exposed to a temperature of 105° C., and weight loss measurements related to the migration of the plasticizer were recorded in intervals of 24 hours (h), 48 h, 72 h and 168 h (a week) after the test started. Comparative example 4 was selected for this test since it is based on phthalate plasticizer, hence a more important comparison from an application standpoint and in structural terms. The resulted weight loss curves obtained from the migration test with the test samples of a compound with the dialkyl esters of 2,4-FDCA of the present disclosure as a plasticizer versus comparative example with DOP are shown in FIG. 3.

Figure 3:
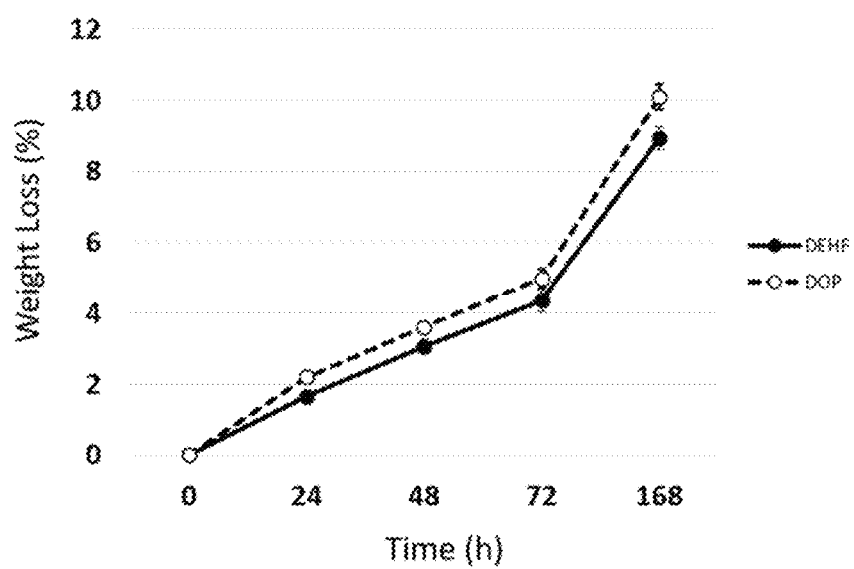
FIG. 3 shows the curves of weight loss obtained from a migration test with the test samples of a compound with the dialkyl esters of 2,4-FDCA of the present disclosure as a plasticizer versus comparative example with DOP.

FIG. 3 demonstrates that the PVC compound prepared with the inventive dialkyl esters of 2,4-FDCA presented overall lower weight loss across the whole experiment when compared to the PVC compound prepared with DOP. Based on structural parameters such as reduced symmetry, presence of branched units and a dipolar moment deriving from the presence of an heteroatom in the central molecular segment of 2,4-DEHF, 2,4-DEHF presents lower relative mobility in the PVC composition when compared to phthalate plasticizers with equivalent pendant side alkyl chain, such as in the comparison above.

In summary, the present inventors surprisingly found that the experimental results of the Shore A hardness shown in FIG. 1 demonstrated that the dialkyl ester of 2,4-FDCA plasticizer of the present disclosure exhibited greater plasticizing efficiency in the PVC compositions than that of the standard phthalate and terephthalate-based plasticizers in the PVC compositions. The present inventor also surprisingly found that the compounds prepared with the inventive plasticizer (the dialkyl esters of 2,4-FDCA) had superior thermal stability and better permanency as compared to the compounds prepared with standard phthalate and terephthalate-based plasticizer, as shown in FIGS. 2 and 3 respectively. The combination of the experimental results demonstrated in FIGS. 1-3 demonstrate the suitability of these new dialkyl esters in terms of performance as plasticizers in polymer compositions and products.

Various changes and modifications to the presently preferred embodiments disclosed herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A compound for plasticizing a polymer material, the compound is a dialkyl ester of 2,4-furandicarboxylic acid (2,4-FDCA) having a chemical structure of Formula I,

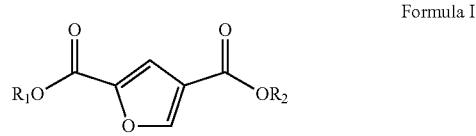

Formula I wherein $R_1$ and $R_2$ each represent an alkyl radical of a $C_5$-$C_{10}$.

2. The compound of claim 1, wherein each of $R_1$ and $R_2$ is an alkyl radical derived from ethylhexanol and the resulting compound is di (ethylhexyl)-2,4-furanoate.

3. The compound of claim 1, wherein $R_1$ is an alkyl radical derived from an alkyl radical of a linear $C_5$-$C_{10}$ monohydric aliphatic primary alcohol.

4. The compound of claim 1, wherein $R_2$ is an alkyl radical derived from an alkyl radical of a linear $C_5$-$C_{10}$ monohydric aliphatic primary alcohol.

5. The compound of claim 1, wherein $R_1$ is an alkyl radical derived from ethylhexanol.

6. The compound of claim 1, wherein $R_1$ is an alkyl radical derived from 2-ethylhexanol.

7. The compound of claim 1, wherein $R_1$ is an alkyl radical derived from isononyl alcohol.

8. The compound of claim 1, wherein $R_1$ is an alkyl radical derived from isodecyl alcohol.

9. The compound of claim 1, wherein $R_1$ is an alkyl radical derived from 2-methyl-1-pentanol.

10. The compound of claim 1, wherein $R_1$ is an alkyl radical derived from 2-propylheptanol.

11. The compound of claim 1, wherein $R_1$ is an alkyl radical derived from isooctyl alcohol.

12. The compound of claim 1, wherein $R_1$ is an alkyl radical derived from amyl alcohol.

13. The compound of claim 1, wherein $R_2$ is an alkyl radical derived from ethylhexanol.

14. The compound of claim 1, wherein $R_2$ is an alkyl radical derived from 2-ethylhexanol.

15. The compound of claim 1, wherein $R_2$ is an alkyl radical derived from isononyl alcohol.

16. The compound of claim 1, wherein $R_2$ is an alkyl radical derived from isodecyl alcohol.

17. The compound of claim 1, wherein $R_2$ is an alkyl radical derived from 2-methyl-1-pentanol.

18. The compound of claim 1, wherein $R_2$ is an alkyl radical derived from 2-propylheptanol.

19. The compound of claim 1, wherein $R_2$ is an alkyl radical derived from isooctyl alcohol.

20. The compound of claim 1, wherein $R_2$ is an alkyl radical derived from amyl alcohol.

* * * * *